United States Patent
Smith et al.

(10) Patent No.: US 12,161,295 B2
(45) Date of Patent: Dec. 10, 2024

(54) DEEP BRAIN STIMULATION ELECTRODE WITH PHOTOACOUSTIC AND ULTRASOUND IMAGING CAPABILITIES

(71) Applicants: Barbara Smith, Scottsdale, AZ (US); Christopher Miranda, Tempe, AZ (US)

(72) Inventors: Barbara Smith, Scottsdale, AZ (US); Christopher Miranda, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1206 days.

(21) Appl. No.: 16/357,074

(22) Filed: Mar. 18, 2019

(65) Prior Publication Data

US 2019/0282069 A1    Sep. 19, 2019

Related U.S. Application Data

(60) Provisional application No. 62/644,344, filed on Mar. 16, 2018.

(51) Int. Cl.
*A61B 1/00* (2006.01)
*A61B 5/00* (2006.01)
(Continued)

(52) U.S. Cl.
CPC ...... *A61B 1/00096* (2013.01); *A61B 1/00002* (2013.01); *A61B 5/0093* (2013.01);
(Continued)

(58) Field of Classification Search
CPC ............ A61B 1/00002; A61B 1/00096; A61B 5/0042; A61B 5/0084; A61B 5/0093;
(Continued)

(56) References Cited

U.S. PATENT DOCUMENTS

| | | | |
|---|---|---|---|
| 4,267,732 A | 5/1981 | Quate | |
| 5,752,518 A * | 5/1998 | McGee | A61B 8/12 600/424 |

(Continued)

FOREIGN PATENT DOCUMENTS

| | | |
|---|---|---|
| CN | 2061692 U | 9/1990 |
| FR | 2997502 A1 | 5/2014 |

(Continued)

OTHER PUBLICATIONS

Craig Freudenrich, "How Fiber Optics Work," Mar. 6, 2001, HowStuffWorks.com, pp. 1-9 (Year: 2001).*
(Continued)

*Primary Examiner* — Joseph M Santos Rodriguez
*Assistant Examiner* — Maria Christina Talty
(74) *Attorney, Agent, or Firm* — Michael Best & Friedrich LLP (57) ABSTRACT

Methods and systems for image-based guidance in deep-brain stimulation. An endoscope system includes a waveguide tube, a right-angle prism, a light source, and a photoacoustic transducer. Light from the light source propagates along the length of the waveguide tube via internal reflection within the wall. The right-angle prism is positioned to redirect light emitted at a distal end of the waveguide tube in a direction perpendicular to the length of the waveguide tube. Light emitted in the perpendicular direction causes soundwaves to be generated by the surrounding tissue via photoacoustic effect. Those soundwaves are then conducted through the interior channel of the waveguide tube from the distal end of the waveguide tube to a proximal end of the waveguide tube where the soundwaves are detected by the photoacoustic transducer, which is acoustically coupled to the interior channel of the waveguide tube at the proximal end of the waveguide tube.

17 Claims, 8 Drawing Sheets

(51) Int. Cl.
*A61N 1/05* (2006.01)
*G02B 27/09* (2006.01)

(52) U.S. Cl.
CPC .......... *A61B 5/0095* (2013.01); *A61N 1/0526* (2013.01); *A61N 1/0529* (2013.01); *A61N 1/0534* (2013.01); *G02B 27/0972* (2013.01)

(58) Field of Classification Search
CPC ...... A61B 5/0095; A61B 8/12; A61N 1/0526; A61N 1/0529; A61N 1/0534; G02B 27/0972; G02B 6/34; G02B 6/3624
See application file for complete search history.

(56) References Cited

U.S. PATENT DOCUMENTS

| | | | |
|---|---|---|---|
| 6,485,413 B1* | 11/2002 | Boppart | G01N 21/4795 600/478 |
| 8,932,223 B2 | 1/2015 | Emelianov et al. | |
| 9,618,445 B2 | 4/2017 | Sun et al. | |
| 10,107,613 B2 | 10/2018 | Jiao et al. | |
| 10,795,440 B1 | 10/2020 | Chevillet et al. | |
| 2007/0299341 A1 | 12/2007 | Wang et al. | |
| 2008/0177183 A1* | 7/2008 | Courtney | G02B 23/2423 600/463 |
| 2010/0079580 A1 | 4/2010 | Waring, IV | |
| 2010/0245766 A1 | 9/2010 | Zhang et al. | |
| 2010/0268042 A1* | 10/2010 | Wang | A61B 5/14546 73/587 |
| 2011/0098530 A1* | 4/2011 | Yamane | A61B 1/00172 600/109 |
| 2011/0282192 A1 | 11/2011 | Axelrod et al. | |
| 2011/0301458 A1 | 12/2011 | Li et al. | |
| 2012/0275262 A1 | 11/2012 | Song et al. | |
| 2013/0158383 A1 | 6/2013 | Cheng et al. | |
| 2013/0216114 A1* | 8/2013 | Courtney | A61B 5/0073 382/128 |
| 2014/0066743 A1 | 3/2014 | Nakajima et al. | |
| 2014/0142404 A1* | 5/2014 | Wang | A61B 8/4444 600/324 |
| 2015/0160168 A1 | 6/2015 | Irisawa | |
| 2015/0226845 A1 | 8/2015 | Witte et al. | |
| 2015/0247999 A1 | 9/2015 | Ntziachristos et al. | |
| 2015/0327768 A1 | 11/2015 | Oyama et al. | |
| 2016/0003777 A1 | 1/2016 | Schmitt-Manderbach et al. | |
| 2016/0143542 A1* | 5/2016 | Bossy | A61B 1/042 600/407 |
| 2016/0235278 A1* | 8/2016 | Goebel | G02B 23/2469 |
| 2016/0242651 A1 | 8/2016 | Wang et al. | |
| 2016/0249812 A1 | 9/2016 | Wang et al. | |
| 2016/0250073 A1 | 9/2016 | Gooding et al. | |
| 2016/0305914 A1 | 10/2016 | Wang et al. | |
| 2016/0356746 A1 | 12/2016 | Piestun et al. | |
| 2017/0055841 A1* | 3/2017 | Mueller | A61B 1/05 |
| 2017/0065182 A1 | 3/2017 | Wang et al. | |
| 2017/0105626 A1 | 4/2017 | Irisawa | |
| 2017/0156600 A1 | 6/2017 | Ntziachristos et al. | |
| 2017/0367682 A1 | 12/2017 | Smith et al. | |
| 2018/0055343 A1* | 3/2018 | Yang | A61B 8/445 |
| 2018/0078143 A1 | 3/2018 | Pramanik et al. | |
| 2018/0132728 A1 | 5/2018 | Wang et al. | |
| 2018/0214119 A1 | 8/2018 | Mehrmohammadi et al. | |
| 2018/0235570 A1* | 8/2018 | Fukushima | A61B 8/12 |
| 2019/0046159 A1 | 2/2019 | Smith et al. | |
| 2019/0110691 A1 | 4/2019 | Smith et al. | |
| 2019/0175938 A1* | 6/2019 | Rezaie | A61B 1/0638 |
| 2019/0227038 A1 | 7/2019 | Wang et al. | |
| 2019/0282069 A1 | 9/2019 | Smith et al. | |
| 2020/0056986 A1 | 2/2020 | Wang et al. | |
| 2020/0160522 A1 | 5/2020 | Merlo et al. | |
| 2020/0173965 A1 | 6/2020 | Sangu | |
| 2020/0340954 A1 | 10/2020 | Smith et al. | |
| 2020/0398268 A1 | 12/2020 | Smith et al. | |
| 2021/0080708 A1 | 3/2021 | Sangu | |
| 2022/0151496 A1 | 5/2022 | Waldner et al. | |

FOREIGN PATENT DOCUMENTS

| | | |
|---|---|---|
| IN | 308501 B | 4/2019 |
| WO | 2008075299 A1 | 6/2008 |
| WO | 2008100386 A2 | 8/2008 |
| WO | 2009050632 A1 | 4/2009 |
| WO | 2015175431 A1 | 11/2015 |
| WO | 2015183092 A1 | 12/2015 |

OTHER PUBLICATIONS

Vasilyev, D.; Merrill, T.; Iwanow, A.; Dunlop, J.; Bowlby, M., A novel method for patch-clamp automation. Pflugers Arch. 2006, 452 (2), 240-247.

Veerman, J. A.; Otter, A. M.; Kuipers, L.; van Hulst, N. F., High definition aperture probes for nearfield optical microscopy fabricated by focused ion beam milling. Applied Physics Letters 1998, 72 (24), 3115-3117.

Wang and S. Hu, "Photoacoustic tomography: in vivo imaging from organelles to organs," Science 335, 1458-1462 (2012).

Wang, A. Karpiouk, D. Yeager, J. Amirian, S. Litovsky, R. Smalling, and S. Emelianov, "Intravascular photoacoustic imaging of lipid in atherosclerotic plaques in the presence of luminal blood," Opt. letters 37, 1244-1246 (2012).

Wang, C.-C.; Hennek, J. W.; Ainla, A.; Kumar, A. A.; Lan, W.- J.; Im, J.; Smith, B. S.; Zhao, M.; Whitesides, G. M., A Paper-Based "Pop-up" Electrochemical Device for Analysis of Beta-Hydroxybutyrate. Analytical Chemistry 2016, 88(12), 6326-6333.

Wang, J. L. Su, A. B. Karpiouk, K. V. Sokolov, R. W. Smalling, and S. Y. Emelianov, "Intravascular photoacoustic imaging," IEEE J. selected topics Quantum Electron. 16, 588-599 (2010).

Wang, L. V., Multiscale photoacoustic microscopy and computed tomography. Nature Photonics 2009, 3 (9), 503-509.

Wang, T. Ma, M. N. Slipchenko, S. Liang, J. Hui, K. K. Shung, S. Roy, M. Sturek, Q. Zhou, Z. Chen, and J.-X. Cheng, "High-speed intravascular photoacoustic imaging of lipid-laden atherosclerotic plaque enabled by a 2-khz barium nitrite raman laser," Sci. reports 4, 6889 (2014).

Wang, X. D.; Pang, Y. J.; Ku, G.; Xie, X. Y.; Stoica, G.; Wang, L. H. V., Noninvasive laser-induced photoacoustic tomography for structural and functional in vivo imaging of the brain. Nat. Biotechnol. 2003, 21 (7), 803-806.

Wang, X. D.; Xie, X. Y.; Ku, G. N.; Wang, L. H. V., Noninvasive imaging of hemoglobin concentration and oxygenation in the rat brain using high-resolution photoacoustic tomography. J. Biomed. Opt. 2006, 11 (2).

Weber, Judith, Paul C. Beard, and Sarah E. Bohndiek. "Contrast agents for molecular photoacoustic imaging." Nature methods 13.8 (2016): 639.

Wong, Terence TW, et al. "Fast label-free multilayered histology-like imaging of human breast cancer by photoacoustic microscopy." Science advances 3.5 (2017): e1602168.

Wu, I. Kolb, B. M. Callahan, Z. Su, W. Stoy, S. B. Kodandaramaiah, R. Neve, H. Zeng, E. S. Boyden, C. R. Forest, and A. A. Chubykin, "Integration of autopatching with automated pipette and cell detection in vitro," J. neurophysiology 116, 1564-1578 (2016).

Xu, Minghua, and Lihong V. Wang. "Photoacoustic imaging in biomedicine." Review of scientific instruments 77.4 (2006): 041101.

Yajuan, X.; Xin, L.; Zhiyuan, L., A comparison of the performance and application differences between manual and automated patch-clamp techniques. Curr Chem Genomics, Jun. 2012, 87-92.

Yang, C. Favazza, J. Yao, R. Chen, Q. Zhou, K. K. Shung, and L. V. Wang, "Three-dimensional photoacoustic endoscopic imaging of the rabbit esophagus," PloS one 10, e0120269 (2015).

Yang, C. Favazza, R. Chen, J. Yao, X. Cai, K. Maslov, Q. Zhou, K. K. Shung, and L. V. Wang, "Simultaneous functional photoacoustic and ultrasonic endoscopy of internal organs in vivo," Nat. medicine 18, 1297-1302 (2012).

Yang, C. Favazza, R. Chen, K. Maslov, X. Cai, Q. Zhou, K. K. Shung, and L. V. Wang, "Volumetric photoacoustic endoscopy of upper gastrointestinal tract: ultrasonic transducer technology development," in Proc. SPIE, , vol. 7899 (2011), pp. 78990D1-78990D6.

(56) References Cited

OTHER PUBLICATIONS

Yang, K. Maslov, H.-C. Yang, Q. Zhou, K. K. Shung, and L. V. Wang, "Photoacoustic endoscopy," Opt. letters 34, 1591-1593 (2009).
Yang, R.; Lai, K. W. C.; Xi, N.; Yang, J., Development of automated patch clamp system for electrophysiology. In 2013 IEEE International Conference on Robotics and Biomimetics, ROBIO 2013, 2013; p. 2185.
Yang, R.; Tam, C. H.; Cheung, K. L.; Wong, K. C.; Xi, N.; Yang, J.; Lai, W. C. K., Cell Segmentation and Pipette Identification for Automated Patch Clamp Recording. Robotics and Biomimetrics 2014, 1 (20), 1-12.
Yao, K. Maslov, K. K. Shung, Q. Zhou, and L. V. Wang, "In vivo label-free photoacoustic microscopy of cell nuclei by excitation of dna and rna," Opt. letters 35, 4139-4141 (2010).
Yizhar, O.; Fenno, L. E.; Davidson, T. J.; Mogri, M.; Deisseroth, K., Optogenetics in Neural Systems. Neuron 2011, 71(1), 9-34.
Zhang and P. C. Beard, "A miniature all-optical photoacoustic imaging probe," in Proc. SPIE, , vol. 7899 (2011), p. 78991F.
Zhang, C.; Maslov, K.; Wang, L. H. V., Subwavelength-resolution label-free photoacoustic microscopy of optical absorption in vivo. Opt. Lett. 2010, 35 (19), 3195-3197.
Zhang, H. F.; Maslov, K.; Stoica, G.; Wang, L. H. V., Functional photoacoustic microscopy for high-resolution and noninvasive in vivo imaging. Nat. Biotechnol. 2006, 24 (7), 848-851.
Zhang, J. Y.; Laiwalla, F.; Kim, J. A.; Urabe, H.; Van Wagenen, R.; Song, Y. K.; Connors, B. W.; Zhang, F.; Deisseroth, K.; Nurmikko, A. V., Integrated device for optical stimulation and spatiotemporal electrical recording of neural activity in ight-sensitized brain tissue. Journal of Neural Engineering 2009, 6 (5).
Zharov, V. P.; Galanzha, E. I.; Shashkov, E. V.; Khlebtsov, N. G.; Tuchin, V. V., In vivo photoacoustic flow cytometry for monitoring of circulating single cancer cells and contrast agents. Opt. Lett. 2006, 31 (24), 3623-3625.
Zharov, V. P.; Galanzha, E. I.; Shashkov, E. V.; Kim, J. W.; Khlebtsov, N. G.; Tuchin, V. V., Photoacoustic flow cytometry: principle and application for real-time detection of circulating single nanoparticles, pathogens, and contrast dyes in vivo. J. Biomed. Opt. 2007, 12 (5).
Zhou, K. H. Lam, H. Zheng, W. Qiu, and K. K. Shung, "Piezoelectric single crystal ultrasonic transducers for biomedical applications," Prog. materials science 66, 87-111 (2014).
Zorzos, A. N.; Boyden, E. S.; Fonstad, C. G., Multiwaveguide implantable probe for light delivery to sets of distributed brain targets. Opt. Lett. 2010, 35 (24), 4133-4135.
Kodandaramaiah, S. B.; Boyden, E. S.; Forest, C. R.; New York Acad, S., In vivo robotics: the automation of neuroscience and other intact-system biological fields. In Conference Reports: Evolutionary Dynamics and Information Hierarchies in Biological Systems: Aspen Center for Physics Workshop and Cracking the Neural Code: Third Annual Aspen Brain Forums, Blackwell Science Publ: Oxford, 2013; vol. 1305, pp. 63-71.
Kodandaramaiah, S. B.; Franzesi, G. T.; Chow, B. Y.; Boyden, E. S.; Forest, C. R., Automated whole-cell patch-clamp electrophysiology of neurons in vivo. Nat. Methods 2012, 9 (6), 585-+.
Kodandaramaish, S. B.; Flores, F. J.; Holst, G. L.; Singer, A. C.; Han, X.; Brown, E. N.; Boyden, E. S.; Forest, C. R., Multi-neuron intracellular recording in vivo via interacting autopatching robots. eLife, Jul. 19, 2018.
Kozodoy, A. T. Pagkalinawan, and J. A. Harrington, "Small-bore hollow waveguides for delivery of 3-mm laser radiation," Appl. optics 35, 1077-1082 (1996).
Ku, G.; Wang, X. D.; Xie, X. Y.; Stoica, G.; Wang, L. H. V., Imaging of tumor angiogenesis in rat brains in vivo by photoacoustic tomography. Applied Optics 2005, 44 (5), 770-775.
Kumar et al., From the Bench to the Field in Low-Cost Diagnostics: Two Case Studies. Angewandte Chemie International Edition 2015, 54 (20), 5836-5853.
LeChasseur, Y.; Dufour, S.; Lavertu, G.; Bories, C.; Deschenes, M.; Vallee, R.; De Koninck, Y., A microprobe for parallel optical and electrical recordings from single neurons in vivo. Nat. Methods 2011, 8 (4), 319-U63.
Tinas, R. R., Intrinsic electrical properties of mammalian neurons and CNS function: a historical perspective. Frontiers in Cellular Neuroscience, Aug. 2014.
Long, L. Li, U. Knoblich, H. Zeng, and H. Peng, "3d image-guided automatic pipette positioning for single cell experiments in vivo," Sci. reports 5, 18426 (2015).
Long, M. A.; Jin, D. Z. Z.; Fee, M. S., Support for a synaptic chain model of neuronal sequence generation. Nature 2010, 468 (7322), 394-399.
Lu, W.; Huang, Q.; Geng, K. B.; Wen, X. X.; Zhou, M.; Guzatov, D.; Brecht, P.; Su, R.; Oraevsky, A.; Wang, L. V.; Li, C., Photoacoustic imaging of living mouse brain vasculature using hollow gold nanospheres. Biomaterials 2010, 31 (9), 2617-2626.
Lusk, Joel F., et al. "Photoacoustic Flow System for the Detection of Ovarian Circulating Tumor Cells Utilizing Copper Sulfide Nanoparticles." ACS Biomaterials Science & Engineering (2019).
Mallidi, S.; Luke, G. P.; Emelianov, S., Photoacoustic imaging in cancer detection, diagnosis, and treatment guidance. Trends in Biotechnology 2011, 29 (5), 213-221.
Margrie, A. H. Meyer, A. Caputi, H. Monyer, M. T. Hasan, A. T. Schaefer, W. Denk, and M. Brecht, "Targeted whole-cell recordings in the mammalian brain in vivo," Neuron 39, 911-918 (2003).
Markram, H.; Lubke, J.; Frotscher, M.; Roth, A.; Sakmann, B., Physiology and anatomy of synaptic connections between thick tufted pyramidal neurones in the developing rat neocortex. Journal of Physiology—London 1997, 500 (2), 409-440.
Maslov, K.; Zhang, H. F.; Hu, S.; Wang, L. V., Optical-resolution photoacoustic microscopy for in vivo imaging of single capillaries. Opt. Lett. 2008, 33 (9), 929-931.
Matsuura, T. Abel, and J. A. Harrington, "Optical properties of smallbore hollow glass waveguides," Appl. optics 34, 6842-6847 (1995).
Matsuura, T. Abel, J. Hirsch, and J. Harrington, "Small-bore hollow waveguide for delivery of near singlemode ir laser radiation," Electron. Lett. 30, 1688-1690 (1994).
Miranda et al., "Side-viewing Photoacoustic Capillary Endoscope," 2018, Optics Letters, 1-4.
Miranda, C.; Barkley, J.; Smith, B. S., Intrauterine photoacoustic and ultrasound imaging probe. J. Biomed. Opt. 2018, 23 (4), 9.
Miranda, Christopher, et al. "Photoacoustic micropipette." Applied Physics Letters 113.26 (2018): 264103.
Neher, E.; Sakmann, B., single-channel currents recorded from membrane of denervated frog muscle-fibers. Nature 1976, 260 (5554), 799-802.
Nichols, J.; Bjorklund, G. R.; Newbern, J.; Anderson, T., Parvalbumin fast-spiking interneurons are selectively altered by paediatric traumatic brain injury. Journal of Physiology—London 2018, 596(7), 1277-1293.
Nichols, J.; Perez, R.; Wu, C.; Adelson, P. D.; Anderson, T., Traumatic Brain Injury Induces Rapid Enhancement of Cortical Excitability in Juvenile Rats. Cns Neuroscience & Therapeutics 2015, 21 (2), 193-203.
Olsen, S. R.; Wilson, R. I., Cracking neural circuits in a tiny brain: new approaches for understanding the neural circuitry of Drosophila. Trends in Neurosciences 2008, 31 (10), 512-520.
Ovsepian, Saak V., et al. "Pushing the boundaries of neuroimaging with optoacoustics." Neuron 96.5 (2017): 966-988.
Papadopoulos, O. Simandoux, S. Farahi, J. Pierre Huignard, E. Bossy, D. Psaltis, and C. Moser, "Optical-resolution photoacoustic microscopy by use of a multimode fiber," Appl. Phys. Lett. 102, 211106 (2013).
Papadopoulos, S. Farahi, C. Moser, and D. Psaltis, "Highresolution, lensless endoscope based on digital scanning through a multimode optical fiber," Biomed. optics express 4, 260-270 (2013).
Patil, Ujwal, et al. "In vitro/in vivo toxicity evaluation and quantification of iron oxide nanoparticles." International journal of molecular sciences 16.10 (2015): 24417-24450.
Pisanello, F.; Sileo, L.; Oldenburg, I. A.; Pisanello, M.; Martiradonna, L.; Assad, J. A.; Sabatini, B.L.; De Vittorio, M., Multipoint-Emitting (56) References Cited

OTHER PUBLICATIONS

Optical Fibers for Spatially Addressable In Vivo Optogenetics. Neuron 2014, 82 (6), 1245-1254.
Richter, D. W.; Pierrefiche, O.; Lalley, P. M.; Polder, H. R., Voltage-clamp analysis of neurons within deep layers of the brain. J. Neurosci. Methods 1996, 67 (2), 121-131.
Rose, G. J.; Alluri, R. K.; Vasquez-Opazo, G. A.; Odom, S. E.; Graham, J. A.; Leary, C. J., Combining pharmacology and whole-cell patch recording from CNS neurons, in vivo. J. Neurosci. Methods 2013, 213 (1), 99-104.
Saiki, T.; Matsuda, K., Near-field optical fiber probe optimized for illumination-collection hybrid mode operation. Applied Physics Letters 1999, 74 (19), 2773-2775.
Schneider, D. M.; Nelson, A.; Mooney, R., A synaptic and circuit basis for corollary discharge in the auditory cortex. Nature 2014, 513 (7517), 189-+.
Sethuraman, S. R. Aglyamov, J. H. Amirian, R. W. Smalling, and S. Y. Emelianov, "Intravascular photoacoustic imaging using an ivus imaging catheter," IEEE transactions on ultrasonics, ferroelectrics, frequency control 54 (2007).
Shi, K. Ito, L. Ma, T. Yoshida, Y. Matsuura, and M. Miyagi, "Fabrication of a polymer-coated silver hollow optical fiber with high performance," Appl. optics 45, 6736-6740 (2006).
Shung, J. Cannata, and Q. Zhou, "Piezoelectric materials for high frequency medical imaging applications: A review," J. Electroceramics 19, 141-147 (2007).
Simandoux, N. Stasio, J. Gateau, J.-P. Huignard, C. Moser, D. Psaltis, and E. Bossy, "Optical-resolution photoacoustic imaging through thick tissue with a thin capillary as a dual optical-in acousticout waveguide," Appl. Phys. Lett. 106, 094102 (2015).
Smetters, D.; Majewska, A.; Yuste, R., Detecting action potentials in neuronal populations with calcium imaging. Methods—a Companion to Methods in Enzymology 1999, 18 (2), 215-221.
Smith, A Shah, Yong-Kyun Lee, B O'Brien, D Kullman, A Sridharan, J Muthuswamy, J B Christen "Optogenetic Neurostimulation of the Auricular Vagus using Flexible OLED Display Technology to Treat Chronic Inflammatory Disease and Mental Health Disorders" Electronics Letters, DOI: 10.1049/el.2015.3450, 2016.
So, P. T. C.; Dong, C. Y.; Masters, B. R.; Berland, K. M., Two-photon excitation fluorescence microscopy. Annual Review of Biomedical Engineering, Feb. 2000, 399-429.
Stasio, A. Shibukawa, I. N. Papadopoulos, S. Farahi, O. Simandoux, J.-P. Huignard, E. Bossy, C. Moser, and D. Psaltis, "Towards new applications using capillary waveguides," Biomed. optics express 6, 4619-4631 (2015).
Stern, E. A.; Kalman, Z.; Lewis, A .; Lieberman, K., simple method for focusing x-rays using tapered capillaries. Applied Optics 1988, 27 (24), 5135-5139.
Stosiek, C.; Garaschuk, O.; Holthoff, K.; Konnerth, A., In vivo two-photon calcium imaging of neuronal networks. Proc. Natl. Acad. Sci. U. S. A. 2003, 100 (12), 7319-7324.
Strohm, E. M.; Moore, M. J.; Kolios, M. C., Single Cell Photoacoustic Microscopy: A Review. Ieee Journal of Selected Topics in Quantum Electronics 2016, 22 (3).
Stuart, G. J.; Dodt, H. U.; Sakmann, B., patch-clamp recordings from the soma and dendrites of neurons in brain-slices using infrared video microscopy. Pflugers Arch. 1993, 423 (5-6), 511-518.
Suk, I. van Welie, S. B. Kodandaramaiah, B. Allen, C. R. Forest, and E. S. Boyden, "Closed-loop real-time imaging enables fully automated cell-targeted patch-clamp neural recording in vivo," Neuron. 95, 1037-1047 (2017).
Svoboda, K.; Yasuda, R., Principles of two-photon excitation microscopy and its applications to neuroscience. Neuron 2006, 50 (6), 823-839.
Timofeev, I.; Grenier, F.; Steriade, M., Disfacilitation and active inhibition in the neocortex during the natural sleep-wake cycle: An intracellular study. Proc. Natl. Acad. Sci. U. S. A. 2001, 98 (4), 1924-1929.
Knight et al., "Hollow-Core Optical Fibers Offer Advantages at Any Wavelength," Photonics Spectra, Apr. 2019.

Abbas, J. J.; Smith, B.; Poluta, M.; Velazquez-Berumen, A., Improving health-care delivery in lowresource settings with nanotechnology:Challenges in multiple dimensions. Nanobiomedicine, Apr. 2017, 1849543517701158.
Abe, Y.-W. Shi, Y. Matsuura, and M. Miyagi, "Flexible small-bore hollow fibers with an inner polymer coating," Opt. letters 25, 150-152 (2000).
Addington, CP, Dharmaraj, S, Heffernan, JM, Sirianni, RW, Stabenfeldt, SE. Hyaluronic acid-laminin hydrogels increase neural stem cell transplant retention and migratory response to SDF-1α. Matrix Biology. 2016;16:30210-4. DOI: 10.1016/j.matbio.2016.09.007.
Anand, S.; Kumar, S. S.; Muthuswamy, J., Autonomous control for mechanically stable navigation of microscale implants in brain tissue to record neural activity. Biomedical Microdevices 2016, 18 (4).
Anderson, T. R.; Hu, B.; Iremonger, K.; Kiss, Z. H. T., Selective attenuation of afferent synaptic transmission as a mechanism of thalamic deep brain stimulation-induced tremor arrest. Journal of Neuroscience 2006, 26 (3), 841-850.
Anderson, T. R.; Huguenard, J. R.; Prince, D. A., Differential effects of Na plus-K plus ATPase blockade on cortical layer V neurons. Journal of Physiology—London 2010, 588 (22), 4401-4414.
Andrasfalvy, B. K.; Galinanes, G. L.; Huber, D.; Barbic, M.; Macklin, J. J.; Susumu, K.; Delehanty, J. B.; Huston, A. L.; Makara, J. K.; Medintz, I. L., Quantum dot-based multiphoton fluorescent pipettes for targeted neuronal electrophysiology. Nat. Methods 2014, 11 (12), 1237-1241.
Annecchino, A. R. Morris, C. S. Copeland, O. E. Agabi, P. Chadderton, and S. R. Schultz, "Robotic automation of in vivo two-photon targeted whole-cell patch-clamp electrophysiology," Neuron 95, 1048-1055 (2017).
Aravanis, A. M.; Wang, L. P.; Zhang, F.; Meltzer, L. A.; Mogri, M. Z.; Schneider, M. B.; Deisseroth, K., An optical neural interface: in vivo control of rodent motor cortex with integrated fiberoptic and optogenetic technology. Journal of Neural Engineering 2007, 4 (3), S143-S156.
Aston-Jones, G.; Deisseroth, K., Recent advances in optogenetics and pharmacogenetics. Brain Research 2013, 1511, 1-5.
Badu-Tawiah, A. K.; Lathwal, S.; Kaastrup, K.; Al-Sayah, M.; Christodouleas, D. C.; Smith, B. S.; Whitesides, G. M.; Bikes, H. D., Polymerization-based signal amplification for paper-based immunoassays. Lab on a chip 2015, 15 (3), 655-659.
Balaic, D. X.; Nugent, K. A., x-ray optics of tapered capillaries. Applied Optics 1995, 34 (31), 7263-7272.
Beard, P., Biomedical photoacoustic imaging. Interface Focus 2011, 1 (4), 602-631.
Beaulieu-Laroche, L.; Harnett, M. T., Dendritic Spines Prevent Synaptic Voltage Clamp. Neuron 2018, 97 (1), 75-82.
Bilderback, D. H.; Fontes, E., Glass capillary optics for making x-ray beams of 0.1 to 50 microns diameter. AIP Conference Proceedings 1997, Medium: X; Size: pp. 147-155.
Billet, A.; Froux, L.; Hanrahan, J. W.; Becq, F., Development of Automated Patch Clamp Technique to Investigate CFTR Chloride Channel Function. Frontiers in Pharmacology Aug. 2017.
Bohndiek, S. Bodapati, D. Van De Sompel, S.-R. Kothapalli, and S. S. Gambhir, "Development and application of stable phantoms for the evaluation of photoacoustic imaging instruments," PloS one 8, e75533 (2013).
Bornstein, J. C.; Furness, J. B., correlated electrophysiological and histochemical-studies of submucous neurons and their contribution to understanding enteric neural circuits. Journal of the Autonomic Nervous System 1988, 25 (1), 1-13.
Boyden, E. S.; Zhang, F.; Bamberg, E.; Nagel, G.; Deisseroth, K., Millisecond-timescale, genetically targeted optical control of neural activity. Nature Neuroscience 2005, 8 (9), 1263-1268.
Chen, C. C.; Cang, C. L.; Fenske, S.; Butz, E.; Chao, Y. K.; Biel, M.; Ren, D. J.; Wahl-Schott, C.; Grimm, C., Patch-clamp technique to characterize ion channels in enlarged individual endolysosomes. Nat. Protoc. 2017, 12 (8), 1639-1658.
Cox, B.; Laufer, J. G.; Arridge, S. R.; Beard, P. C., Quantitative spectroscopic photoacoustic imaging: a review. J. Biomed. Opt. 2012, 17 (6).

(56) References Cited

OTHER PUBLICATIONS

Cullen, D. K.; Stabenfeldt, S. E.; Simon, C. M.; Tate, C. C.; LaPlaca, M. C., In vitro neural injury model for optimization of tissue-engineered constructs. Journal of Neuroscience Research 2007, 85 (16), 3642-3651.
De La Zerda, Adam, et al. "Carbon nanotubes as photoacoustic molecular imaging agents in living mice." Nature nanotechnology 3.9 (2008): 557.
Deisseroth, K., Optogenetics. Nat. Methods 2011, 8 (1), 26-29.
Desai, N. S.; Siegel, J. J.; Taylor, W.; Chitwood, R. A.; Johnston, D., MATLAB-based automated patch-clamp system for awake behaving mice. Journal of Neurophysiology 2015, 114 (2), 1331-1345.
Dika et al., Early experiences and integration in the persistence of first-generation college students in STEM and non-STEM majors. Journal of Research in Science Teaching 2016, 53 (3), 368-383.
Dunn, R. C., Near-field scanning optical microscopy. Chemical reviews 1999, 99 (10), 2891-2928.
Fan, B.; Li, W., Miniaturized optogenetic neural implants: a review. Lab on a Chip 2015, 15 (19), 3838-3855.
Fenno, L.; Yizhar, O.; Deisseroth, K., The Development and Application of Optogenetics. In Annual Review of Neuroscience, vol. 34, Hyman, S. E.; Jessell, T. M.; Shatz, C. J.; Stevens, C. F.; Zoghbi, H. Y., Eds. 2011; vol. 34, pp. 389-412.
Frow, E. K.; Smith, B. S.; Ankeny, C. J. In Freshman design course: Device design for low-resource settings, ASEE Annual Conference and Exposition, Conference Proceedings, 2017.
Galanzha, E. I.; Shashkov, E. V.; Spring, P. M.; Suen, J. Y.; Zharov, V. P., In vivo, Noninvasive, Label-Free Detection and Eradication of Circulating Metastatic Melanoma Cells Using Two-Color Photoacoustic Flow Cytometry with a Diode Laser. Cancer Research 2009, 69 (20), 7926-7934.
Goddeyne, C.; Nichols, J.; Wu, C.; Anderson, T., Repetitive mild traumatic brain injury induces ventriculomegaly and cortical thinning in juvenile rats. Journal of Neurophysiology 2015, 113 (9), 3268-3280.
Gooch, C. L.; Pracht, E.; Borenstein, A. R., The burden of neurological disease in the United States: A summary report and call to action. Annals of neurology 2017, 81 (4), 479-484.
Grewe, B. F.; Langer, D.; Kasper, H.; Kampa, B. M.; Helmchen, F., High-speed in vivo calcium imaging reveals neuronal network activity with near-millisecond precision (vol. 7, p. 399, 2010). Nat. Methods 2010, 7 (6), 479-479.
Hamill, O. P.; Marty, A.; Neher, E.; Sakmann, B.; Sigworth, F. J., improved patch-clamp techniques for high-resolution current recording from cells and cell-free membrane patches. Pflugers Arch. 1981, 391 (2), 85-100.
Harvey, C. D.; Collman, F.; Dombeck, D. A.; Tank, D. W., Intracellular dynamics of hippocampal place cells during virtual navigation. Nature 2009, 461 (7266), 941-U196.
Hayar, A. Gu, and E. D. Al-Chaer, "An improved method for patch clamp recording and calcium imaging of neurons in the intact dorsal root ganglion in rats," J. neuroscience methods 173, 74-82 (2008).
Hecht, B.; Sick, B.; Wild, U. P.; Deckert, V.; Zenobi, R.; Martin, O. J. F.; Pohl, D. W., Scanning near-field optical microscopy with aperture probes: Fundamentals and applications. Journal of Chemical Physics 2000, 112 (18), 7761-7774.
Helmchen, F.; Denk, W., Deep tissue two-photon microscopy. Nat. Methods 2005, 2 (12), 932-940.
Hu, S.; Maslov, K.; Wang, L. V., Second-generation optical-resolution photoacoustic microscopy with improved sensitivity and speed. Opt. Lett. 2011, 36 (7), 1134-1136.
Hurtado, S.; Newman, C. B.; Tran, M. C.; Chang, M. J., Improving the Rate of Success for Underrepresented Racial Minorities in STEM Fields: Insights from a National Project. New Directions for Institutional Research 2010, 148, 5-15.
Ishitani, T. T., Studying attrition and degree completion behavior among first-generation college students in the United States. The Journal of Higher Education 2006, 77 (5), 861-885.
Jansen, M. Wu, A. F. van der Steen, and G. van Soest, "Lipid detection in atherosclerotic human coronaries by spectroscopic intravascular photoacoustic imaging," Opt. express 21, 21472-21484 (2013).
Karpiouk, B. Wang, J. Amirian, R. W. Smalling, and S. Y. Emelianov, "Feasibility of in vivo intravascular photoacoustic imaging using integrated ultrasound and photoacoustic imaging catheter," J. biomedical optics 17, 0960081-0960086 (2012).
Keene, A. C.; Waddell, S., *Drosophila* olfactory memory: single genes to complex neural circuits. Nature Reviews Neuroscience 2007, 8 (5), 341-354.
Khraiche, W Phillips, N Jackson, J Muthuswamy, "Sustained Elevation of Activity of Developing Neurons Grown on Polyamide Microelectrode Arrays (MEA) in Response to Ultrasound Exposure," Microsystem Technologies, doi:10.1007/s00542-016-3150-6, 2016.
Kim, E. Chung, H. Yamashita, K. E. Hung, A. Mizoguchi, R. Kucherlapati, D. Fukumura, R. K. Jain, and S. H. Yun, "In vivo wide-area cellular imaging by side-view endomicroscopy," Nat. methods 7, 303 (2010).
Kim, Taeho et al. "Photoacoustic Imaging of Human Mesenchymal Stem Cells Labeled with Prussian Blue-Poly(I-lysine) Nanocomplexes." ACS nano vol. 11,9 (2017): 9022-9032. doi:10.1021/acsnano.7b03519.
Kitamura, B. Judkewitz, M. Kano, W. Denk, and M. Hausser, "Targeted patch-clamp recordings and single-cell electroporation of unla-beled neurons in vivo," Nat. methods 5, 61-67 (2008).
Kodandaramaiah, G. L. Holst, I. R. Wickersham, A. C. Singer, G. T. Franzesi, M. L. McKinnon, C. R. Forest, and E. S. Boyden, "Assembly and operation of the autopatcher for automated intracellular neural recording in vivo," Nat. protocols 11, 634-654 (2016).
United States Patent Office Action for U.S. Appl. No. 16/159,167 dated Mar. 23, 2021 (15 pages).
Kuck, N., et al. "Visible electroluminescent subwavelength point source of light." Applied physics letters 61.2 (1992):139-141.
Thor Labs "Achromatic Pairs" 2011 (Year: 2011) (3 pages).

* cited by examiner

DEEP BRAIN STIMULATION ELECTRODE WITH PHOTOACOUSTIC AND ULTRASOUND IMAGING CAPABILITIES

RELATED APPLICATIONS

This application claims the benefit of U.S. Provisional Patent Application No. 62/644,344, filed Mar. 16, 2018, entitled "PHOTOACOUSTIC AND ULTRASOUND ENDOSCOPIC IMAGING USING A SIDE-VIEWING HOLLOW OPTICAL WAVEGUIDE," the entire contents of which are incorporated herein by reference.

BACKGROUND

The present invention relates to systems and methods for endoscopic imaging. In particular, some implementations relate to systems and methods of real-time visual guidance for deep brain stimulation.

When deep brain stimulation is performed, it is often done with very little visual guidance and no real-time visual guidance. In some cases, the patient will undergo MRI imaging to calculate the relative distance between the point of entry of the electrode (e.g., through a hole in the skull) and the area of the brain to be stimulated. A frame is drilled to the patient's head which is then used to guide the electrode to the appropriate area of the brain as determined by information from the MRI imaging data. The surgeon slowly advances the electrode towards a deep area of the brain while using the electrode to measure the electrical activity of the brain. In some cases, the electrical activity is compared to known electrical activity of different areas of the brain to provide the surgeon with further information about the location of the electrode in the brain.

SUMMARY

Some embodiment disclosed herein include electrodes similar to those currently available for deep-brain stimulation with added internal photoacoustic and ultrasound imaging components that enable 360-degree scanning of the region perpendicular to the axis of the electrode. These real-time scans are then displayed to a surgeon to see where a probe is located relative to the skull (using ultrasound imaging) and relative to the surrounding brain tissue (using photoacoustic imaging).

A photoacoustic and ultrasound imaging electrode has the potential to change the way deep-brain stimulation is performed. Due to the complexity and inherent danger in the procedure, the added benefit of real-time imaging information would lead to a vast improvement in this type of brain surgery.

In some embodiments, the invention provides (1) combined ultrasound and photoacoustic imaging with an electrode and (2) placement of a transducer for photoacoustic imaging outside the electrode probe. Because the transducer is positioned outside of the probe, it remains outside of the patient's skull during the procedure. In some embodiments, the electrode probe includes one or more straight rods that are also configured to operate as tunnels for ultrasound—something not currently applicable to other ultrasound imaging probes. In various embodiments, this configuration also provides the added benefit of real-time imaging feedback as well as electrical feedback typically used to guide electrode placement in deep-brain stimulation.

In some embodiments, the system is configured to emit light for photoacoustic analysis. While existing technologies can typically only peer less than 5 mm deep into the brain, systems and methods disclosed herein can be used to provide photoacoustic imaging at depths of up to 1-3 cm into the brain.

In one embodiment, the invention provides an endoscope system including a waveguide tube, a right-angle prism, a light source, and a photoacoustic transducer. The light source is coupled to the wall of the waveguide tube at a proximal end of the waveguide tube such that light from the light source propagates along the length of the waveguide tube via internal reflection within the wall. The right-angle prism is positioned at a distal end of the waveguide tube and configured to redirect light emitted at a distal end of the waveguide tube in a direction perpendicular to the length of the waveguide tube. Light emitted in the perpendicular direction causes soundwaves to be emitted by the surrounding tissue via photoacoustic effect. The interior channel of the waveguide tube is configured to conduct those soundwaves from the distal end of the waveguide tube to a proximal end of the waveguide tube where the soundwaves are detected by the photoacoustic transducer, which is acoustically coupled to the interior channel of the waveguide tube at the proximal end of the waveguide tube.

In another embodiment, the invention provides a method of operating a deep-brain stimulation probe. A light source is activated, which causes light to enter the wall of a waveguide tube and to propagate along the length of the waveguide tube via total internal reflection within the wall. This light is emitted at a distal end of the waveguide tube where it is then redirected by a right-angle prism in a direction perpendicular to the length of the waveguide tube. The perpendicularly emitted light causes the surrounding tissue to generate soundwaves through the photoacoustic effect and those soundwaves are conducted through an interior channel of the waveguide tube to a photoacoustic transducer that is acoustically coupled to the interior channel at a proximal end of the waveguide tube. The photoacoustic soundwaves are detected by the photoacoustic transducer and, based at least in part on photoacoustic image data, it is determined whether the deep-brain stimulation probe is positioned at a target location in the brain. In response to a determination that the probe is positioned at the target location, a stimulation circuit is activated to apply the deep-brain stimulation.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Photoacoustic endoscopy (PAE) can be useful as a minimally invasive tool for imaging internal organs and tissues. The photoacoustic effect is generated when photons are absorbed by select targets, thus resulting in thermoelastic expansion and the creation of a subsequent acoustic wave. A transducer (often located within the endoscope itself) is used to detect acoustic waves. Previous applications of PAE have successfully provided imaging of the vasculature along the esophagus and intestines, plaque in large arteries, and the lining of the uterus. Due in part to the size of the transducer, these PAE systems typically employ the use of imaging probes with diameters on the order of a few millimeters. For certain applications where the imaging probe is required to be minimally invasive, however, further minimization is necessary. One approach may be to attempt to reduce the size of the transducer. However, because the resulting signal-to-noise ratio of the system is often dependent on the size of the transducer, the approach of reducing the size of the transducer has limitations in in-vivo applications where deep-tissue and/or low frequency transducers are required. Another notable effect of transducer miniaturization is the decreased range of working frequencies. Accordingly, imaging probes may be constrained to shallow imaging depths (e.g., no greater than a few millimeters).

Various implementations described herein circumvent these issues, in part, by providing PAE architectures that provide light transmission and sound detection on a significantly smaller size scale. For example, in some implementations, hollow optical waveguides are configured to concentrically guide both light and sound on a smaller and less-invasive size scale. Due to their material properties (i.e., borosilicate glass and quartz glass), capillaries can be used as hollow optical waveguides. These capillary tubes can be efficiently coupled to a light source such that the light travels along the glass wall of the capillary tube by total internal reflection. Transducers are coupled to the water-filled center of a hollow optical waveguide thereby enabling sound to travel several centimeters along the length of a capillary with minimal attenuation.

Furthermore, to combine the benefits of traditional side-viewing PAE with the miniaturization of hollow optical waveguides, some implementations described herein provide side-viewing photoacoustic capillary endoscopes (PCE). This design readily enables miniaturization without the need for highly specialized transducers. The water-filled hollow center of the PCE can be coupled to transducers of virtually any size or frequency. Thus, insertion of the hollow optical waveguide into tissue provides for light delivery and sound detection at distances exceeding the depth of penetration for visible light and high-frequency ultrasound. Rotation of the probe allows for a 360-degree photoacoustic reconstruction with imaging depths approaching a centimeter.

In some implementations, the PCE architecture described herein also enables integration of light delivery along with acoustic detection without obstructing either. This is accomplished through the use of an optical and acoustic combiner located externally to the PCE and up to several centimeters from the imaging window. Thus, any noise that may be generated as a result of incident light on the transducer occurs well before acquisition of the signals of interest. PAE systems with improper optical and acoustic separation may lead to ultrasound transducers being exposed to excitation light, resulting in bright rings in image reconstructions. This results in poor signal-to-noise ratio for photoacoustic signals acquired near the imaging window. With a relatively inexpensive fabrication, the PCE is an ideal candidate for a myriad of pre-clinical and clinical applications where typical PAE systems are impractical, due to their size. As a result of the efficiency of PCE in transmitting both light and sound, further imaging modalities including fluorescence and pulse-echo ultrasound imaging may still be incorporated into the device.

Figure 1:
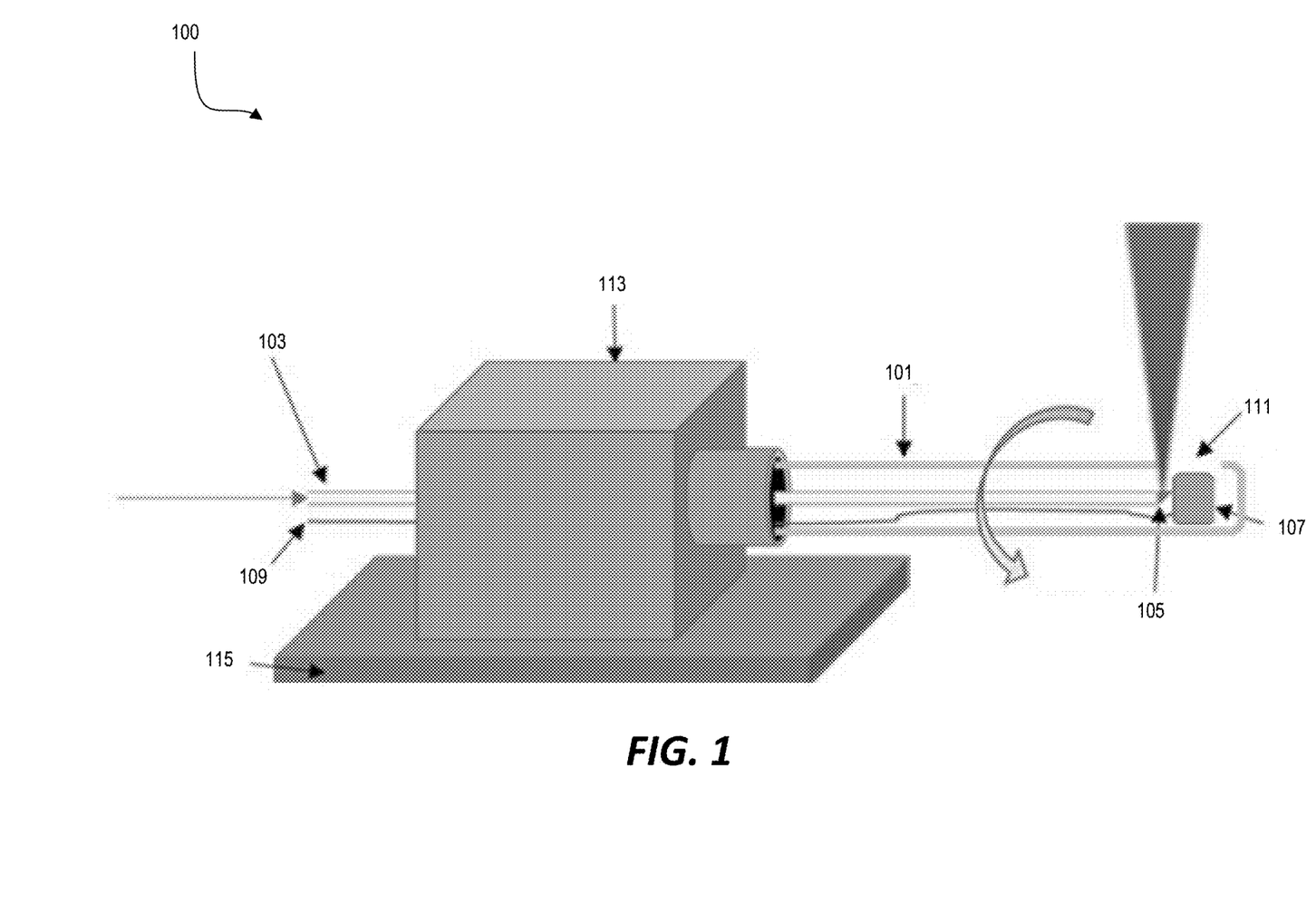
FIG. 1 is a perspective view of a deep-brain stimulation system equipped for photoacoustic and ultrasound imaging-based guidance according to one embodiment.

FIG. 1 illustrates an example of a system including a photoacoustic capillary endoscope. The system of FIG. 1 include a probe for deep-brain stimulation and is also equipped for both photoacoustic imaging and ultrasound imaging. The system 100 includes a clear plastic housing 101 with the capillary waveguide 103 positioned therein. A right-angle prism or mirror 105 is positioned at the distal end of the capillary waveguide 103 and, as described in further detail below, is configured to project light for photoacoustic imaging in a direction perpendicular to the capillary waveguide 103 and to redirect returning sound waves through the water-filled interior channel of the capillary waveguide 103. The system 100 also includes a 15 MHz ultrasound transducer 107 positioned at the distal end of the probe housing 101 beyond the distal end of the capillary waveguide 103. A signal wire 109 is communicatively coupled to the ultrasound transducer 107 and runs alongside the capillary waveguide 103 to the proximal end of the probe housing 101 where it is coupled to the image processing system (e.g., a computer as described in further detail below).

In the example of FIG. 1, the probe housing 101 includes a sound aperture 111 that allows sound waves to enter the probe housing 101 for photoacoustic imaging and allows sound waves to enter and exit the probe housing 101 for ultrasound imaging. In the example of FIG. 1, the sound aperture 111 is shown as an opening in the probe housing 101; however, as described in further detail below, in some implementations, the aperture 111 may be covered with another material (e.g., tubing) that is more sound-permeable than the probe housing 101 while also sealing the interior of the probe housing 101.

The probe housing 101 is coupled to a rotational stage 113. The rotational stage 113 includes a motor for controllably rotating the probe housing about a center axis of the probe housing 101. By controllably rotating the probe housing 101, the rotational stage 113 allows the system to capture ultrasound and photoacoustic image data in 360-degrees about the distal end of the probe housing 101 (e.g., at the sound aperture 111). The system of FIG. 1 also includes a linear stage 115 with a linear motor configured to controllably adjust a linear position of the probe housing 101 in an x and/or y direction. In this way, the linear stage 115 may be controllably operated to insert and retract the probe housing 101 into the anatomy (e.g., into the patient's skull for deep-brain stimulation).

Figure 2:
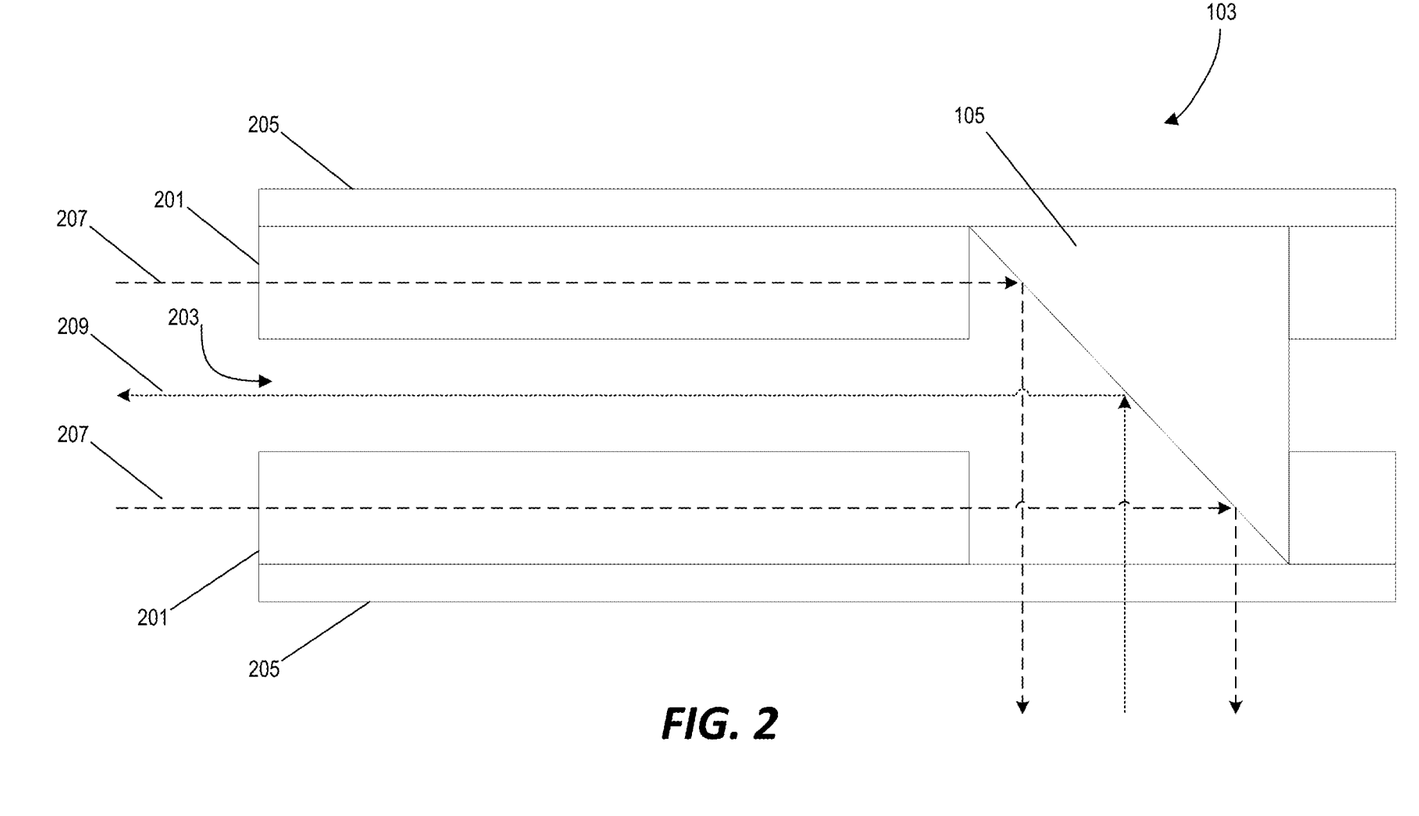
FIG. 2 is a cross-sectional view of a capillary waveguide for photoacoustic imaging in the system of FIG. 1.

FIG. 2 illustrates a cross-section of the capillary waveguide 103. The capillary waveguide 103 includes a hollow cylindrical tube 201 formed of borosilicate glass with an interior channel 203. In the example of FIG. 2, the borosilicate glass of the cylindrical tube 201 is 125 µm thick and the diameter of the interior channel 203 is 750 µm. The interior channel 203 is filled with water or another sound-conducting medium. The exterior surface of the hollow cylindrical tube 201 is enclosed in a 6 µm-thick medical tubing 205. A right-angle prism 105 is positioned at the distal end of the hollow cylindrical tube 201 and enclosed in the medical tubing 205.

In this example, the hollow cylindrical tube 201 is a borosilicate glass capillary tube, B100-75-10, e.g., provided by Sutter Instrument, and the medical tubing 205 is medical tubing 103-0552, e.g., provided by Vention Medical. The right-angle prism 105 is provided as an aluminum-coated right angle prism (MPCH-1.0, Tower Optical). However, in other implementations, the size and material of these components may be different. Similarly, in the example of FIG. 2, the interior channel 203 of the hollow cylindrical tube 201 is filled with water. However, in other implementations, the interior channel 203 may be filled with another gaseous, liquid, or solid sound-conducting material.

Light 207 from an external source (e.g., a laser light source as described in detail below) is projected into the glass material of the hollow cylindrical tube 201 and propagates along the length of the hollow cylindrical tube 201 by total internal reflection. At the distal end of the hollow cylindrical tube 201, the light 207 exits the glass material and is reflected by the right-angle prism 105 in a direction perpendicular to the length of the hollow cylindrical tube 201. The projected light 207 causes sound 209 to be returned from the tissue material due to the photoacoustic effect. The sound 209 is also reflected by the right-angle prism 105 and propagates through the interior channel 203 along the length of the hollow cylindrical tube 201.

Figure 3:
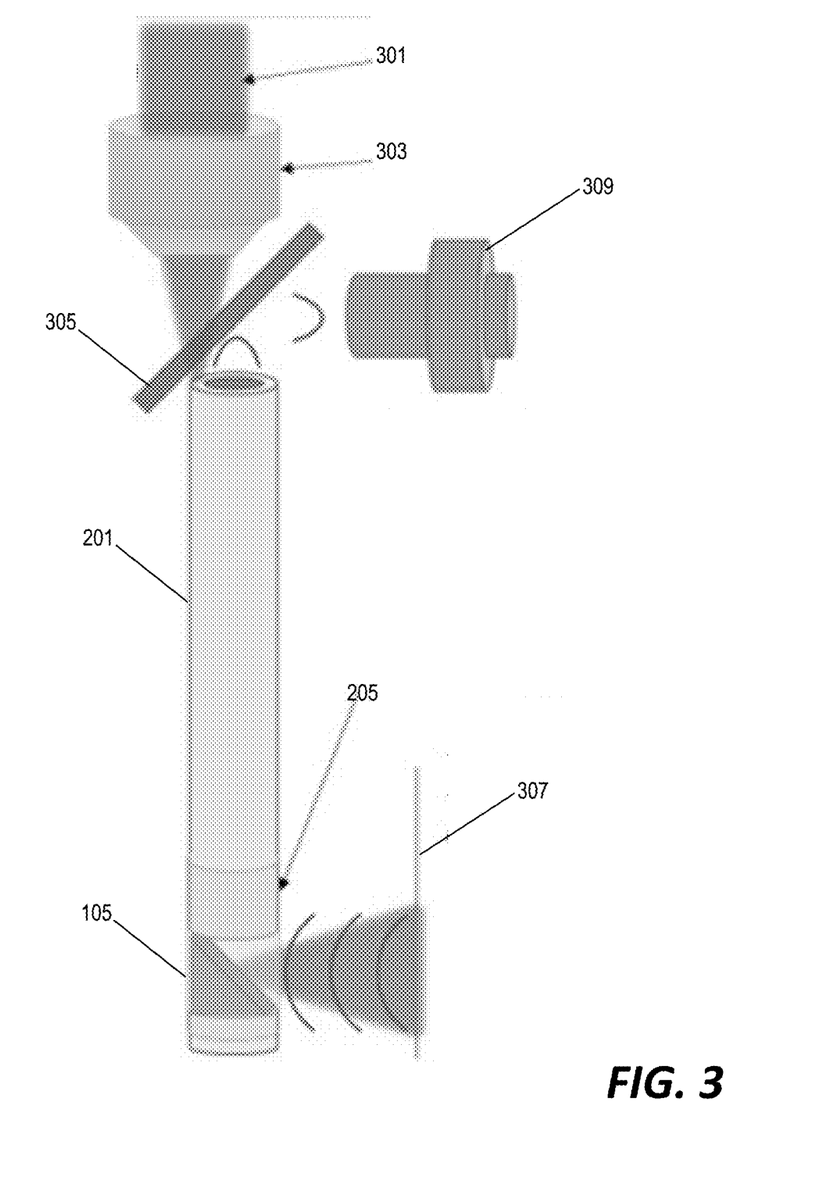
FIG. 3 is a schematic diagram of light projection and sound detection mechanisms for photoacoustic imaging using the capillary waveguide of FIG. 2 in the system of FIG. 1.

FIG. 3 further demonstrates the operation of the capillary waveguide in the photoacoustic imaging operation of the system of FIG. 1. In the example of FIG. 3, a light beam 301 is generated by a light source (e.g., a tunable LS-2134-LT30 Nd:YAG/Ti:Sapphire nanosecond pulsed laser, e.g., provided by Symphotic TII Corporation, operating at a 532 nm wavelength). The laser provides an excitation light with a full width half maximum (FWHM) of 12-15 ns at a pulse repetition rate of 10 Hz. Light is focused into a multimode optical fiber using a 10× objective with a 0.25 NA (LMH-10×-532, e.g., provided by Thorlabs). In the example of FIG. 3, the optical fiber (not pictured) is coupled to the glass wall layer of the hollow cylindrical tube 201 by refocusing light onto the glass wall using a second 10× objective 303 with a 0.25 NA (LMH-10×-1064, e.g., provided by Thorlabs). Light travels along the glass wall of the hollow cylindrical tube 201 by total internal reflection, where it is ultimately redirected by the right angle prism 105 through optically clear medical tubing 205. Light exits perpendicular to the orientation of the device, where it can induce the photoacoustic effect on a select target 307. Resulting photoacoustic signals travel through the acoustically-clear medical tubing 205 and along the water-filled core of the hollow cylindrical tube 201 to a 10 Mhz transducer 309 with a focal length of 1.27 cm, element diameter of 6 mm, and a −6 dB fractional bandwidth of 99.9% (A312S-SU, e.g., provided by Olympus) positioned at the proximal end of the device. The distance the sound travels from the transducer to the top of the capillary tube is equal to the focal length of the transducer. A 1 mm thick glass slide 305 is positioned at a 45-degree angle to the axis of the hollow cylindrical tube 201 and enables both optical and acoustic coupling. The glass slide 305 redirects sound exiting the hollow cylindrical tube 201 toward the center of the transducer 309 while having minimal effects on the excitation light 301 coupled to the glass wall of the hollow cylindrical tube 201.

Photoacoustic signals detected by the transducer 309 are sent to an ultrasound pulser/receiver (5077PR, Olympus Inc.), where amplification is performed through a 59 dB gain and filtered with a 1 MHz high-pass filter. Data acquisition is performed with a multipurpose reconfigurable oscilloscope (NI PXIe-5170R, National Instruments Corporation) and transferred to a computer for image reconstruction. The multipurpose reconfigurable oscilloscope has built-in programmable function input/output (PFI) lines controlled by a built-in field programmable gate array (FPGA) allowing for custom triggering and synchronization of the system.

Again, FIG. 3 provides just one example of a configuration for photoacoustic imaging using a capillary waveguide. Other configurations, components, and positionings are possible. Similarly, the specific materials and components described above are only one specific example. Other system components, computing devices, amplifiers, etc. can be incorporated in other implementations.

Figure 4:
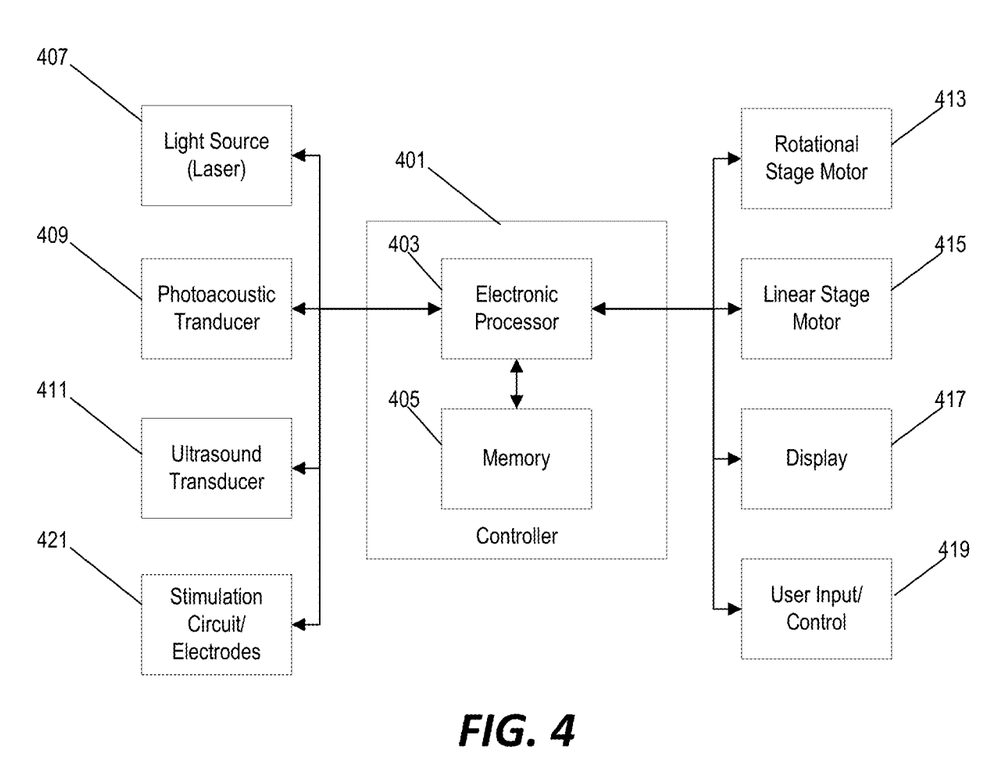
FIG. 4 is a block diagram of a control system for performing photoacoustic imaging, ultrasound imaging, and deep-brain stimulation using the system of FIG. 1.

FIG. 4 provides a simplified block diagram of a system for performing deep-brain stimulation with photoacoustic and ultrasound imaging-guidance using the system of FIG. 1. The system includes a controller 401 with an electronic processor 403 and a non-transitory computer-readable memory 405. The memory 405 stores data (e.g., image data) and instructions that are executed by the electronic processor 403 to provide certain functionality of the system. The controller 401 is communicative coupled to a light source 407 (e.g., a laser source) and a photoacoustic transducer 409. Accordingly, the controller 401 is able to operate the photoacoustic imaging by controllably operating the light source 407 and monitoring the output of the photoacoustic transducer 409. The controller 401 is also communicatively coupled to an ultrasound transducer 411 for ultrasound imaging.

The controller 401 is communicatively coupled to a rotational stage motor 413 to controllably rotate the probe housing during 360-degree imaging and is communicatively coupled to a linear stage motor 415 to controllably adjust an insertion depth of the probe housing. The controller 401 receives data from the photoacoustic transducer 409 and the ultrasound transducer 411, generates photoacoustic and/or ultrasound images from the received data, and output the generated image on a display screen 417. The controller 401 may also be coupled to a user input/control 419 through which a user may control the operation of the system. The insertion depth of the probe housing may be adjusted either manually (e.g., through the display 417 and user input control 419) or automatically based on the captured image data and, once the probe is placed at an appropriate depth proximal to a target tissue, the controller 401 regulates the operation of a stimulation circuit/electrodes 421 to provide deep-brain stimulation.

Figure 5A:
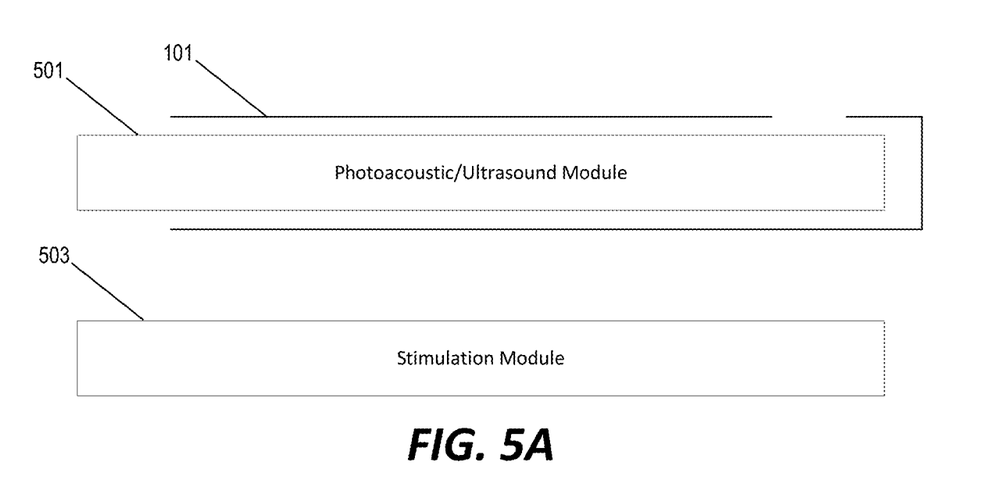
FIG. 5A is a modular configuration of the system of FIG. 1 equipped for placement of the probe using image-based guidance.
Figure 5B:
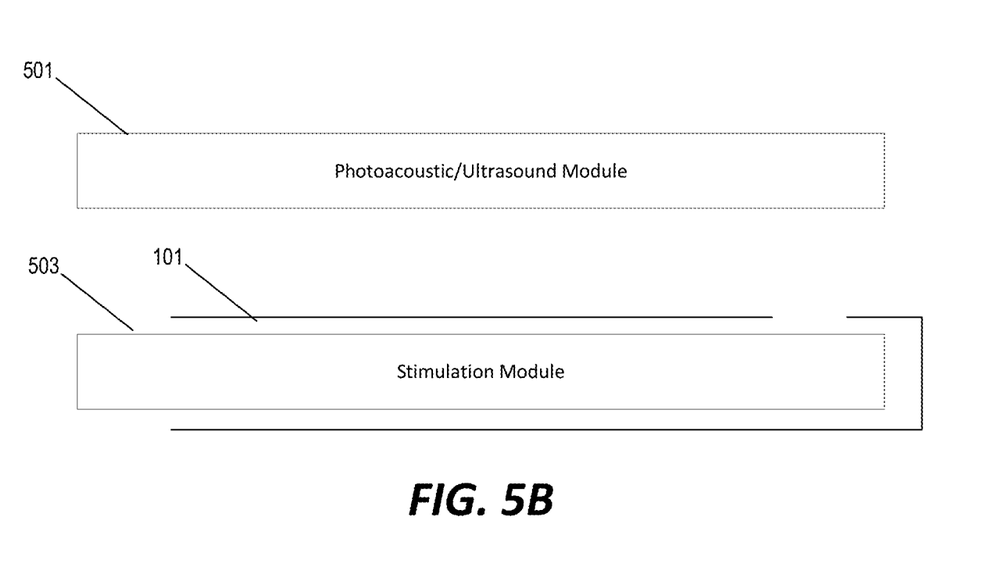
FIG. 5B is the modular configuration of the system of FIG. 1 equipped for deep-brain stimulation after placement of the probe.

In the example of FIG. 1, both the ultrasound imaging components and the photoacoustic imaging components are provided in the same probe housing at the same time. As described above, in some implementations, the stimulation circuit and/or electrodes are also incorporated into the same probe housing with the imaging components to provide deep-brain stimulation when the probe housing is positioned at the appropriate target location. In other implementations, the system is provided as a modular configuration such that an imaging module can be selectively removed through the proximal end of the probe housing once the probe housing is positioned at a target location and a stimulation module can be inserted. FIGS. 5A and 5B illustrate one example of such a modular configuration. In the example of FIG. 5A, the photoacoustic/ultrasound module 501 is inserted into the probe housing 101 for real-time image-based guidance for placement of the probe housing 101. In FIG. 5A, the entire stimulation module 503 has been removed from the probe housing 101. Once the probe housing 101 has been placed at the appropriate target location (as confirmed via the image-based guidance), the photoacoustic/ultrasound module 501 is removed from the probe housing 101 and replaced with the stimulation module 503 as shown in FIG. 5B. In the example of FIGS. 5A and 5B, the probe housing 101 is not moved as the modules are interchanged and remains positioned at the target location for deep-brain stimulation. Accordingly, the photoacoustic/ultrasound module 501 can be used for image-based guidance to achieve proper placement of the probe housing 101 and, once, proper placement is achieved & verified, the stimulation module 503 is inserted for deep-brain stimulation at the proper target location.

Figure 6:
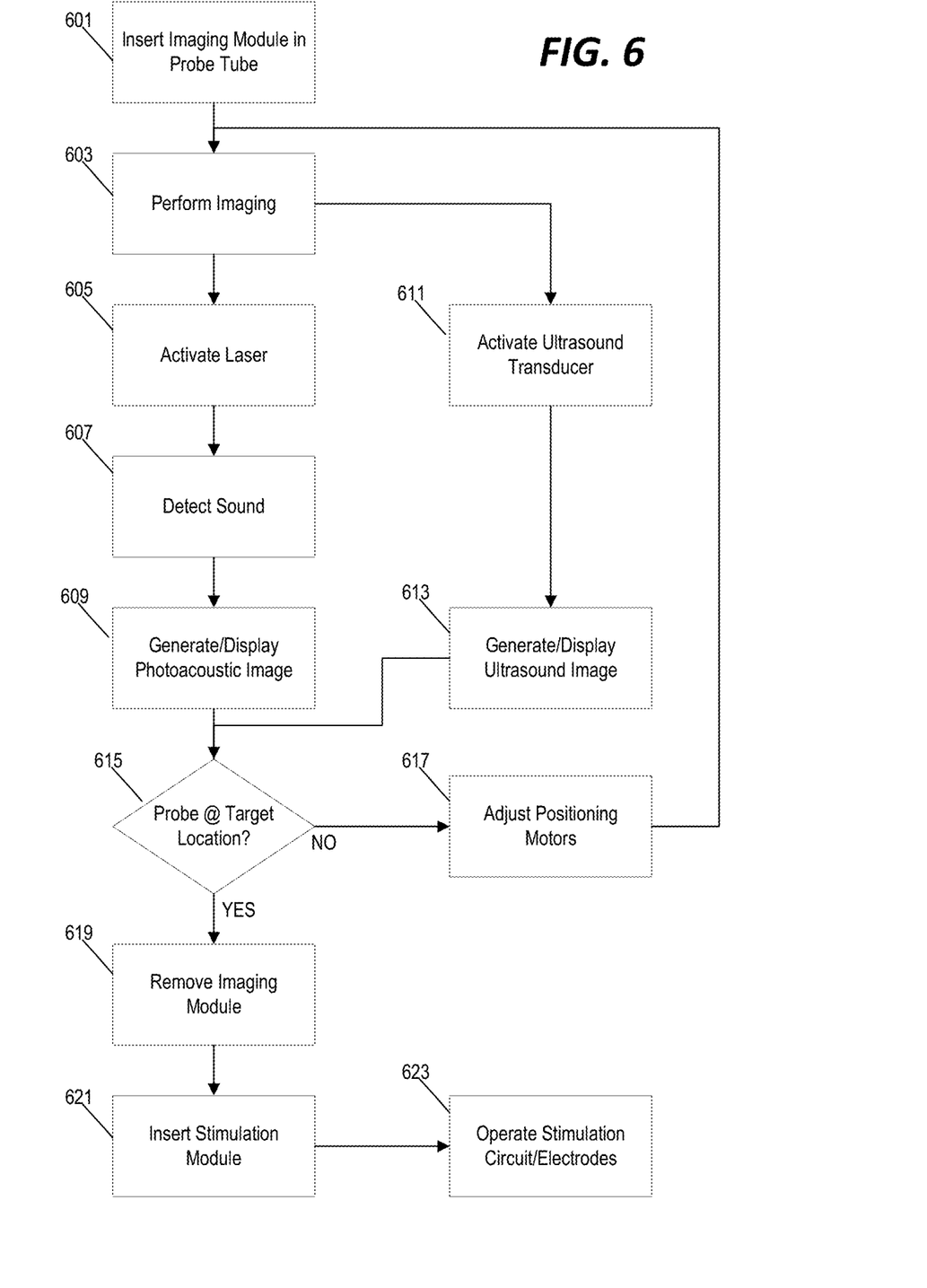
FIG. 6 is a flowchart of a method for image-based guidance and deep-brain stimulation using the system of FIG. 1 and the modular configurations of FIGS. 5A and 5B.

FIG. 6 illustrates a method for performing deep-brain stimulation using the modular system of FIGS. 5A and 5B. First, the imaging module 501 is inserted into the probe housing 101 (step 601). As the probe housing 101 is advanced into the brain tissue, imaging is performed (step 603). For photoacoustic imaging, the laser is activated (step 605), sound generated by the photoacoustic effect is detected through the transducer 309, and photoacoustic image data is probe housing 101 is generated/displayed to the user (step 609). For ultrasound imaging, the ultrasound transducer 107 is appropriately controlled & monitored (step 611) and ultrasound images are displayed (step 613). For both imaging modalities, the probe housing is controllably rotated to provide for 360-degree imaging. The generated image data provides real-time image-based guidance for the placement of the probe housing. In some implementations, a user views the generated images and manually determines whether the probe has reached its target location (e.g., target insertion depth) (step 615). In other implementations, the system is configured to analyze the captured image data and to automatically determine whether the probe housing has reached its target location. In still other implementations, the system is configured to provide automatic guidance while prompting the user to make the final determination of whether the probe housing has reached its target location. In some implementations, image data alone is used to determine whether the probe housing has reached its target location. In other implementations, image data is used in combination with other data (e.g., electrical signals from brain electrodes as discussed above) to determine positioning of the probe housing in the anatomy.

If the probe housing has not yet reached its target location (step 615), the controller continues to operate the linear stage motors (step 617) and continues to perform imaging (step 603) until the target location is reached. Once the probe is positioned at the appropriate target location, the imaging module is removed (step 619) and the stimulation module is inserted into the probe housing (step 621). With the position of the probe housing confirmed, at least in part, by the image data, and the stimulation module in place, the controller then operates the stimulation circuit to provide deep-brain stimulation (step 623).

The example of FIG. 6 utilizes the modular component configuration of FIGS. 5A and 5B. In some implementations, the system may be configured to output a manual instruction to the user to remove and/or insert a particular system module. In other implementations, the system may be configured to automatically retract and insert individual modules into the probe housing based on a user instruction and/or an operating state of the system. For example, the system may be configured to automatically retract the imaging module and to automatically insert the stimulation module in response to automatically determining (based at least in part on the imaging data) that the probe housing has reached its target location.

Furthermore, certain functionality as illustrated in FIG. 6 may be adapted to implementations that do not include modular construction. For example, if the system is provided with the imaging components and stimulation components permanently positioned in the probe housing, the system may be configured to perform imaging, adjust the positioning of the probe, and perform the deep-brain stimulation as illustrated in the example of FIG. 6 without the instruction or automated steps for removing and/or inserting the various modules.

To demonstrate the imaging capabilities of the system described above, the imaging device is introduced into the hollow center of a cylindrical polyvinyl chloride plastisol (PVCP, M-F Manufacturing) phantom tissue and scanned from within. Line targets, embedded in the PVCP phantom tissues, are radially scanned using the methods described above. The PVCP phantom tissues are fabricated according to methods demonstrated previously, with minor adjustments. In brief, 90 mL of PVCP is poured into a round bottom flask, submerged in an oil bath at 220 C. The mixture is allowed to heat for approximately 9 minutes while stirring under vacuum. PVCP is transferred to a glass cylinder mold with a protruding center and parallel line targets. The PVCP is allowed to remain in the mold until it reaches room temperature and solidifies. The cylindrical phantom tissue has an outer diameter of 3.8 cm, inner diameter of 3 mm, and line targets embedded. The embedded target lines consist of either carbon fiber threads with a 7.2 mm diameter are positioned approximately 1 mm from the center of the mold, or carbon fiber rods with a 254 mm diameter are positioned approximately 6.5 to 8 mm from the center. The probe housing of FIG. 1 is submerged in distilled water inside a custom built tank. A small hole, located at the bottom of the tank allows the imaging end of the capillary to be inserted into the water-filled hollow center of the phantom, which sits on the motorized stage. After each photoacoustic data acquisition the stage rotates 0.45 degrees, enabling a 360 degree 2D scan of the phantom tissue.

Figure 7A:
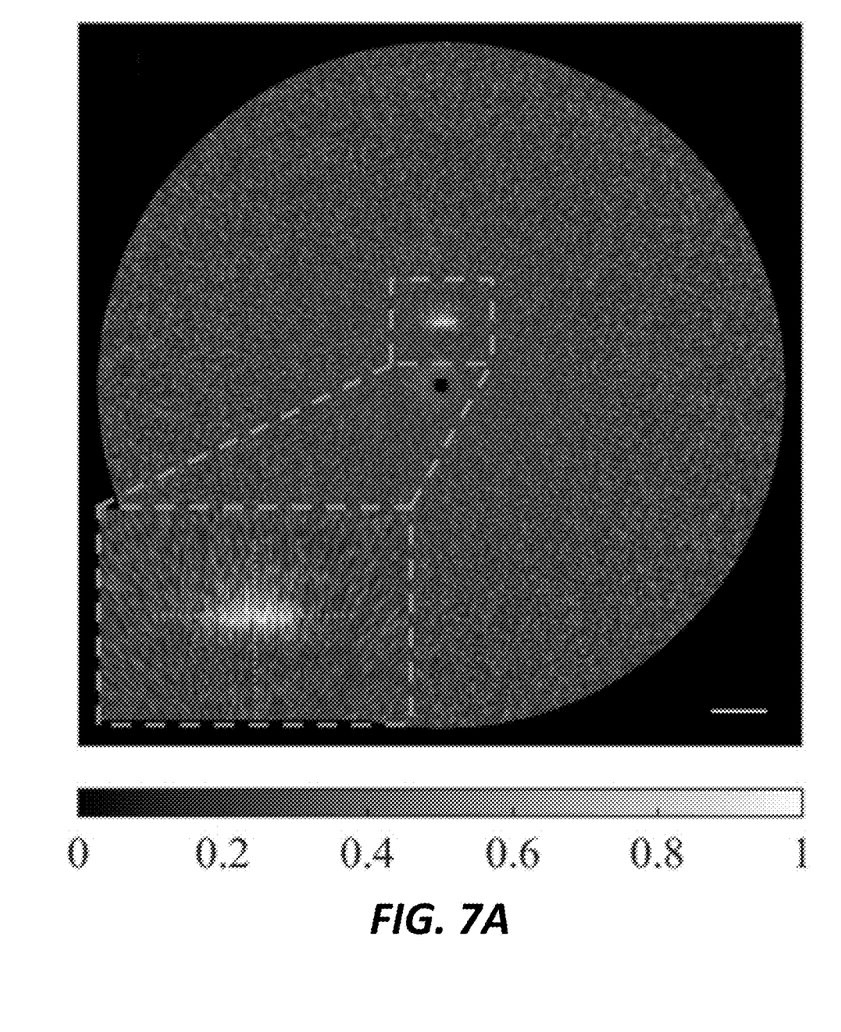
FIG. 7A is an ultrasound image generated by image data captured by the system of FIG. 1.
Figure 7B:
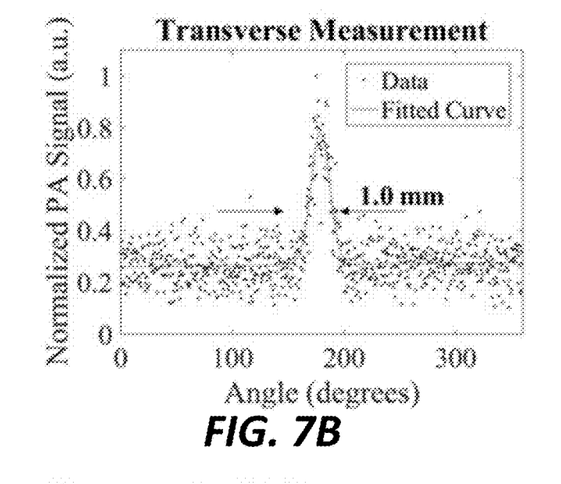
FIG. 7B is a graph of ultrasound image data of FIG. 7A as a function of angular position of the rotating probe demonstrating transverse resolution measurement.
Figure 7C:
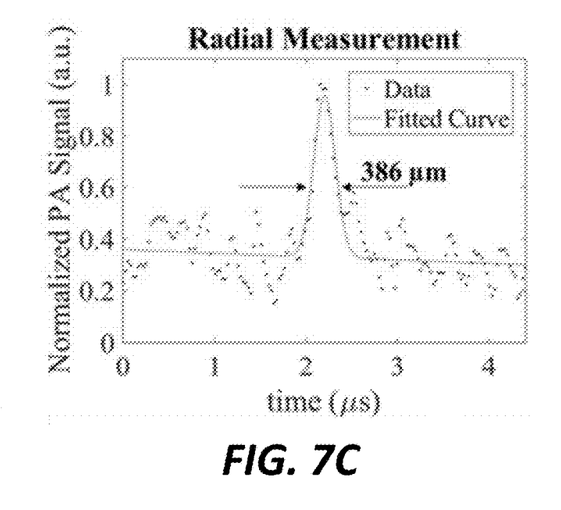
FIG. 7C is a graph of ultrasound image data of FIG. 7A as a function of time as the probe is rotated demonstrating radial resolution of the peak signal in FIG. 7B.

FIGS. 7A, 7B, and 7C illustrates photoacoustic image data acquired using the capillary waveguide of FIG. 2 with an external illumination source positioned on an opposite side of the carbon fiber thread from the capillary waveguide. The optical fiber is oriented perpendicularly to the imaging probe, aligned with the imaging window of the capillary waveguide, and positioned roughly 1 mm from the outer surface of the phantom tissue. A portion of the sound generated from the photoacoustic effect travels toward the capillary waveguide, through the acoustically clear medical tubing, where it is then redirected by the right angle prism. Sound is able to travel along the roughly 5.5 cm length of the capillary tube such that the sound exits into the water tank toward the combiner, where it is ultimately redirected toward the transducer, resulting in an A-line acquisition. This is done at 800 angular positions spanning a total of 360 degrees. A Hilbert Transform is applied to each A-line acquisition and the complex magnitude is subsequently calculated, normalized, and converted into a series of pixel values. Each processed A-line is compressed to a total of 500 representative data points by averaging clusters of numbers together, thus resulting in representative A-lines with fewer data points. Using a look-up table format, each data point is assigned a group of pixels using a weighted average, resulting in an image reconstruction, as shown in FIG. 7A. Measurements of the 7.2 mm diameter line target are performed in both the transverse and radial direction. A maximum signal is identified at each angular step, normalized, and plotted, as shown in FIG. 7B. The transverse FWHM is measured to be 1.0 mm using a Gaussian fit and a radial distance of 3 mm from the PCE. Radial resolution measurements were performed on the A-line acquired at the angular step that provided the maximum signal, as shown in FIG. 7C. Using a Gaussian fit, the radial resolution measurement shows a FWHM of 386 mm using a speed of sound in the phantom of 1400 m/s.

Figure 8A:
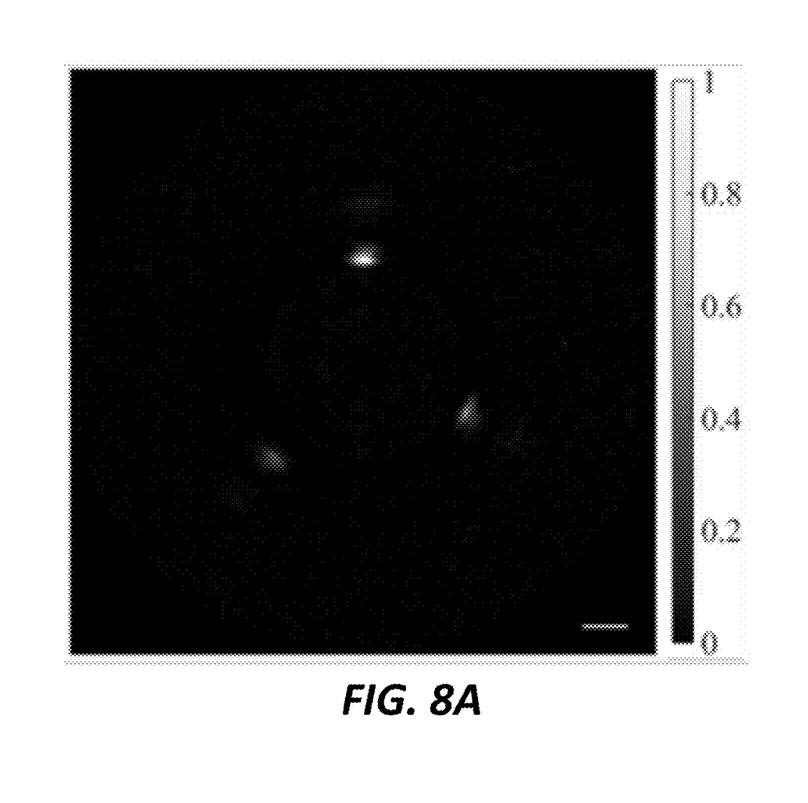
FIG. 8A is a photoacoustic image generated by image data captured by the system of FIG. 1.
Figure 8B:
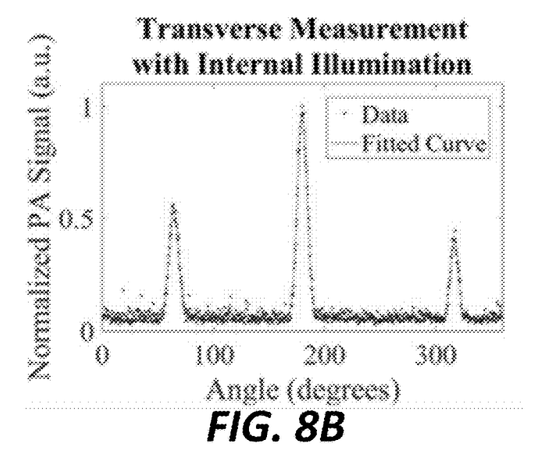
FIG. 8B is a graph of the photoacoustic image data of FIG. 8A showing the maximum amplitude at each angular position of the rotating probe.
Figure 8C:
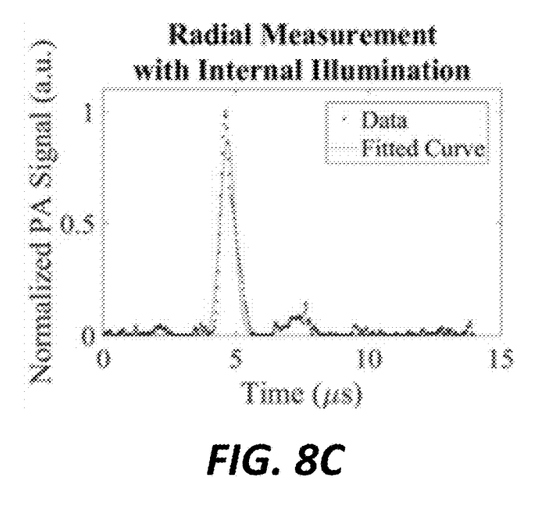
FIG. 8C is a graph of the photoacoustic image data of FIG. 8A showing the radial data corresponding to the maximum signals of FIG. 8B.

FIGS. 8A, 8B, and 8C illustrate photoacoustic reconstruction using internal illumination (as illustrated in FIGS. 2 and 3). In this example, a phantom was constructed with three 254 μm diameter carbon fiber rods. FIG. 8A illustrates the image data captured by the photoacoustic imaging. Due to a drop in coupling efficiency between the optical fiber and the glass wall of the hollow cylindrical tube, less light is able to illuminate the targets using internal illumination. However, the carbon fiber rods are still detectable in the resulting photoacoustic image data. The reconstruction also shows an echo artifact of the carbon fiber rods. This echo emerges as a result of the 3 mm inner diameter chamber of the phantom. At each angular step of the 360 degree scan, the maximum value is calculated and plotted, as shown in FIG. 8B. In order to avoid artificial widening of the FWHM, the aforementioned echo artifacts were not included in these calculations.

The mean photoacoustic transverse FWHM is calculated to be 1.8 mm when using external illumination. Distances from the hollow cylindrical tube for each of the rods varied between 6.5 to 8.0 mm from the imaging probe. For internal illumination, the transverse FWHM is calculated to be 1.2 mm. The drop in the FWHM is likely due to the drop in excitatory light that occurred as a result of the drop in laser coupling efficiency to the glass wall of the hollow cylindrical tube. Measurements in the radial direction are performed using the singular angular position corresponding to the maximum peaks from each of the carbon fiber rods. For internal illumination, the mean FWHM in the radial direction is calculated to be 849 μm. A representative signal using internal illumination is shown in FIG. 8C, which corresponds to the largest peak in FIG. 8B.

Thus, the invention provides, among other things, systems and methods for real-time in-vivo photoacoustic imaging using a capillary waveguide and a photoacoustic transducer positioned outside of the probe housing. In some implementations, the invention provides systems and methods of image-based guidance for deep-brain stimulation. Various features and advantages of the invention are set forth in the following claims.

What is claimed is:

1. An endoscope system comprising:
a tubular probe housing;
a waveguide tube including a wall layer, the wall layer forming a hollow cylindrical tube around a fluid-filled interior channel, the waveguide tube positioned inside the tubular probe housing;
a right-angle prism positioned at a distal end of the waveguide tube;
a light source coupled to the wall layer of the waveguide tube at a proximal end of the waveguide tube;
wherein the coupling of the light source and the wall layer of the waveguide tube causes light emitted from the light source to propagate along a length of the wall layer via internal reflection within the wall layer;
wherein the right-angle prism is configured to redirect light emitted at a distal end of the waveguide tube in a direction perpendicular to the length of the waveguide tube;
a photoacoustic transducer acoustically coupled to the fluid-filled interior channel of the waveguide tube at the proximal end of the waveguide tube;
wherein fluid in the fluid-filled interior channel of the waveguide tube is configured to conduct soundwaves generated by photoacoustic effect caused by the light emitted in the direction perpendicular to the length of the waveguide tube from the distal end of the waveguide tube to the proximal end of the waveguide tube where the soundwaves are detected by the photoacoustic transducer;
an ultrasound transducer positioned inside the tubular probe housing on an opposite side of the right-angle prism than the waveguide tube, the ultrasound transducer configured to transmit sound waves into anatomy and receive reflected sound waves to generate an image identifying where the tubular probe housing is located relative to the anatomy; and
a controller operatively coupled to the photoacoustic transducer and operatively coupled to the ultrasound transducer, wherein the controller is configured to:
generate real-time photoacoustic image data based on signals from the photoacoustic transducer, wherein the photoacoustic image data is indicative of a position of the tubular probe housing relative to brain tissue, and
generate real-time ultrasound image data based on signals from the ultrasound transducer, wherein the ultrasound image data is indicative of a position of the tubular probe housing relative to a skull.

2. The endoscope system of claim 1, wherein the coupling of the light source and the wall layer of the waveguide tube is configured to propagate light from the light source along the length of the waveguide tube by total internal reflection within the wall layer of the waveguide tube.

3. The endoscope system of claim 1, wherein the interior channel of the waveguide tube is water-filled.

4. The endoscope system of claim 1, wherein a portion of the waveguide tube and the right-angle prism are enclosed in an exterior tubing that is both acoustically transparent and optically transparent.

5. The endoscope system of claim 4, wherein the photoacoustic transducer is positioned outside of the exterior tubing and is acoustically coupled to the interior channel of the waveguide tube at a proximal end of the exterior tubing.

6. The endoscope system of claim 1, further comprising one or more electrodes for deep-brain stimulation.

7. The endoscope system of claim 6, further comprising:
a linear stage configured to controllably adjust an insertion depth of the tubular probe housing; and
wherein the controller is further configured to:
determine, based at least in part on photoacoustic image data, whether the tubular probe housing is positioned at a target location for deep-brain stimulation,
controllably operate the linear stage to advance the tubular probe housing in response to determining that the tubular probe housing is not positioned at the target location, and
apply deep-brain stimulation through the one or more electrodes in response to determining that the tubular probe housing is positioned at the target location.

8. The endoscope system of claim 1, further comprising:
a rotational stage configured to rotate the tubular probe housing along an axis parallel to a length of the tubular probe housing; and
wherein the controller is further configured to configured to perform photoacoustic imaging by:
activating the light source,
measuring photoacoustic soundwaves via the photoacoustic transducer, and
controllably rotating the tubular probe housing for 360-degree side-view photoacoustic imaging.

9. The endoscope system of claim 1, wherein the right-angle prism is further configured to reflect soundwaves into the internal channel of the waveguide tube, wherein the reflected soundwaves enter the waveguide tube from the direction perpendicular to the length of the waveguide tube.

10. The endoscope system of claim 1, further comprising:
a glass slide positioned at the proximal end of the waveguide tube;
wherein the glass slide is configured to reflect soundwaves from the fluid-filled interior channel of the waveguide tube in a first direction towards the photoacoustic transducer; and
wherein the glass slide is positioned in an optical path between the light source and the wall of the waveguide tube and is configured to transmit the light from the light source towards the wall layer of the waveguide tube.

11. The endoscope system of claim 1, wherein the wall layer includes a glass capillary tube.

12. The endoscope system of claim 11, wherein the wall layer is formed of borosilicate glass.

13. A method of operating a deep-brain stimulation probe, the method comprising:
activating a light source, wherein the light source is optically coupled to a wall layer of a waveguide tube causing light from the light source to propagate along a length of the waveguide tube via total internal reflection within the wall layer of the waveguide tube and to be emitted at a distal end of the waveguide tube where the emitted light is redirected by a right-angle prism in a direction perpendicular to the length of the waveguide tube, wherein the right-angle prism is positioned at a distal end of the waveguide tube, wherein the wall layer of the waveguide tube forms a hollow cylindrical tube around a fluid-filled interior channel;
detecting soundwaves through a photoacoustic transducer, wherein the photoacoustic transducer is acoustically coupled to the fluid-filled interior channel of the waveguide tube, and wherein fluid within the fluid-filled channel of the waveguide tube is configured to conduct soundwaves from photoacoustic effect caused by the light emitted in the direction perpendicular to the length of the waveguide tube;
activating an ultrasound transducer to transmit ultrasound waves to a patient brain in the direction perpendicular to the length of the waveguide tube and to receive reflected ultrasound waves to generate real-time ultrasound image data, wherein the ultrasound transducer is positioned inside a tubular probe housing on an opposite side of the right-angle prism than the waveguide tube;
determining, based at least in part on real-time photoacoustic image data from an output of the photoacoustic transducer and the real-time ultrasound image data, whether the deep-brain stimulation probe is positioned at a target location in the patient brain, wherein the real-time photoacoustic image data is indicative of a position of the deep-brain stimulation probe relative to brain tissue, wherein the real-time ultrasound image data is indicative of a position of the deep-brain stimulation probe relative to a skull; and
activating a stimulation circuit to apply deep-brain stimulation after determining that the deep-brain stimulation probe is positioned at the target location.

14. The method of claim 13, further comprising:
generating a photoacoustic image based on the output of the photoacoustic transducer;
outputting the photoacoustic image to a display screen; and
operating a linear stage to advance the deep-brain stimulation probe based on a first user-initiated instruction;
wherein activating the stimulation circuit to apply the deep-brain stimulation includes activating the stimulation circuit in response to a second user-initiated instruction received after the photoacoustic image is output to the display screen.

15. The method of claim 13, further comprising:
removing an imaging module through a proximal end of the deep-brain stimulation probe in response to determining that the deep-brain stimulation probe is positioned at the target location; and
inserting a stimulation module through the proximal end of the deep-brain stimulation probe after removing the imaging module in response to determining that the deep-brain stimulation probe is positioned at the target location;
wherein an external housing of the deep-brain stimulation probe is not moved while the imaging module is removed and the stimulation module is inserted.

16. An endoscope system comprising:
a tubular probe housing;
a light source;
an imaging module removably insertable into the tubular probe housing at a proximal end of the tubular probe housing, the imaging module including:

a waveguide tube including a wall layer, the wall layer forming a hollow cylindrical tube around a fluid-filled interior channel, the wall layer coupled to the light source, a right-angle prism positioned at a distal end of the waveguide tube, a photoacoustic transducer acoustically coupled to the fluid-filled interior channel of the waveguide tube at the proximal end of the waveguide tube, wherein the light source is coupled to the wall layer of the waveguide tube at a proximal end of the waveguide tube, wherein the coupling of the light source and the wall layer of the waveguide tube causes light from the light source to propagate along a length of the waveguide tube via internal reflection within the wall, wherein the right-angle prism is configured to redirect light emitted at a distal end of the waveguide tube in a direction perpendicular to the length of the waveguide tube, wherein fluid in the fluid-filled interior channel of the waveguide tube is configured to conduct soundwaves generated by photoacoustic effect caused by the light emitted in the direction perpendicular to the length of the waveguide tube from the distal end of the waveguide tube to the proximal end of the waveguide tube where the soundwaves are detected by the photoacoustic transducer, and an ultrasound transducer positioned on a side of the right-angle prism opposite the waveguide tube, the ultrasound transducer configured to transmit ultrasound waves in the direction perpendicular to the length of the waveguide tube and receive reflected ultrasound waves;

a stimulation module including one or more electrodes for deep-brain stimulation, wherein the stimulation module is removably insertable into the tubular probe housing at the proximal end of the tubular probe housing; and a controller operatively coupled to the photoacoustic transducer and operatively coupled to the ultrasound transducer, wherein the controller is configured to:

generate real-time photoacoustic image data based on signals from the photoacoustic transducer, wherein the photoacoustic image data is indicative of a position of the tubular probe housing relative to brain tissue, and generate real-time ultrasound image data based on signals from the ultrasound transducer, wherein the ultrasound image data is indicative of a position of the tubular probe housing relative to a skull.

17. The endoscope system of claim 16, wherein the imaging module is removable through the proximal end of the tubular probe housing and the stimulation module is insertable through the proximal end of the tubular probe housing while the tubular probe housing is positioned in vivo without moving the tubular probe housing.

* * * * *